(12) United States Patent
Ebisawa et al.

(10) Patent No.: US 7,999,215 B2
(45) Date of Patent: Aug. 16, 2011

(54) IMAGE READING APPARATUS HAVING DUAL WHITE REFERENCE PLATE AND IMAGE READING METHOD FOR EFFECTIVELY PERFORMING SHADING COMPENSATION

(75) Inventors: Takashi Ebisawa, Wakaguri (JP); Yukio Yoshikawa, Wakaguri (JP)

(73) Assignee: Riso Kagaku Corporation, Tokyo (JP)

( * ) Notice: Subject to any disclaimer, the term of this patent is extended or adjusted under 35 U.S.C. 154(b) by 290 days.

(21) Appl. No.: 12/453,808

(22) Filed: May 22, 2009

(65) Prior Publication Data

US 2009/0294701 A1    Dec. 3, 2009

(30) Foreign Application Priority Data

May 27, 2008   (JP) .................. 2008-138504
Mar. 12, 2009  (JP) .................. 2009-059800

(51) Int. Cl.
*H01L 27/00*        (2006.01)
(52) U.S. Cl. .................. 250/208.1; 250/205
(58) Field of Classification Search .............. 250/208.1, 250/205, 234, 235, 214 C; 358/461–475, 358/483–486, 494–497; 355/75–83
See application file for complete search history.

(56) References Cited

U.S. PATENT DOCUMENTS 7,525,693 B2 *   4/2009   Matsumoto ............... 358/461

FOREIGN PATENT DOCUMENTS

JP   2002-033915   1/2002

* cited by examiner

*Primary Examiner* — Que T Le
(74) *Attorney, Agent, or Firm* — The Nath Law Group; Jerald L. Meyer; Derek Richmond

(57) ABSTRACT

When reading the first document sheet, light intensity reference data is acquired by sampling a white reference plate while acquiring light intensity reference auxiliary data indicative of the light intensity of a light source lamp by sampling an auxiliary white reference plate. Then, just before reading the second or subsequent sheet, the auxiliary white reference plate is sampled to acquire the latest light intensity auxiliary data, followed by calculating the change amount from the light intensity reference auxiliary data. The change amount is used to correct the light intensity reference data separately for each picture element by referring to the profile data in which is stored the change amount of the sample value of each picture element corresponding to the change amount of the light intensity, followed by performing the shading compensation. By this configuration, it is possible to perform shading compensation in correspondence with the actual light intensity reduction.

20 Claims, 8 Drawing Sheets

IMAGE READING APPARATUS HAVING DUAL WHITE REFERENCE PLATE AND IMAGE READING METHOD FOR EFFECTIVELY PERFORMING SHADING COMPENSATION

BACKGROUND OF THE INVENTION

1. Field of the Invention

The present invention generally relates to an image reading apparatus and an image reading method, and more particularly relates to the technique of reducing the time required for shading compensation and improving the throughput of reading document sheets.

2. Description of the Background Art

In an image reading apparatus, shading compensation is performed for the purpose of preventing an image from being unevenly read due to variations in the light intensity of a light source lamp and time-dependent change thereof, the sensitiveness dispersion of image reading elements and so forth. The shading compensation is performed by sampling a white reference plate provided in the image reading apparatus with a width which is greater than or equal to the main scan width to acquire white reference values and prepare compensation data for each picture element. Then, the image of a document sheet is captured followed by compensating the densities of the image in accordance with the compensation data.

Japanese Patent Published Application No. 2002-33915 discloses a simplified shading compensation technique which avoids throughput degradation which results from the step of sampling a white reference plate each time the document sheet is read. In this simplified shading compensation technique, when a first document reading process is performed, the white reference plate is sampled to perform ordinary shading compensation, but the read data of the subsequent document reading process is compensated by measuring the light intensity of the light source lamp without sampling the white reference plate, on the basis of the reduction of the light intensity from the light intensity measured when the first document reading process is performed.

Generally speaking, while a small auxiliary white reference plate is provided separate from the white reference plate, the light intensity of the light source lamp is measured by reading the small auxiliary white reference plate by some of image reading elements. In the case of the image reading apparatus provided with an automatic document feeder which is capable of reading document sheets without need for moving a light source lamp, the throughput of reading document sheets can be further improved by providing an auxiliary white reference plate located in a position where it can be read without need for moving the light source lamp from the document reading position.

The simplified shading compensation technique described in Japanese Patent Published Application No. 2002-33915 is performed by the use of the white reference values which are acquired when the first document reading process is performed, and then uniformly adjusted in accordance with the reduction of the light intensity after the first document reading process.

However, the reduction of the light intensity sometimes varies along the main scanning direction due to the characteristics of the light source lamp, the differences of temperature in the vicinity of the light source lamp under the influence of the airflow, for example, generated by cooling fan, and so forth. Because of this, the technique of uniformly adjusting the sample values of the white reference plate measured when the first document reading process is performed based on the reduction of the light intensity cannot always be correctly adjusted in proportion to the actual reduction of the light intensity.

SUMMARY OF THE INVENTION

Taking into consideration the above circumstances, it is an object of the present invention to provide an image reading apparatus capable of performing shading compensation to the light intensity reduction of a light source lamp by correcting the sample values of a white reference plate in accordance with the actual light intensity reduction.

In order to accomplish the object as described above, an image reading apparatus in accordance with a first aspect of the present invention is provided with a light source and an image sensor having a plurality of light sensing elements arranged in the main scanning direction, and operable to irradiate an object to be read with light emitted from the light source and read the reflected light from the object by the image sensor, and comprises: a white reference plate having a length which is no shorter than the main scanning width of the image sensor; an auxiliary white reference plate which is smaller than the white reference plate; a storing unit operable to store differential profile data indicative of a time-dependent change amount of the light intensity on the white reference plate detected by each of the light sensing elements corresponding to a time-dependent change amount of the light intensity of the light source, and differential profile auxiliary data indicative of a time-dependent change amount of a light intensity on the auxiliary white reference plate read by the image sensor as a representative light intensity of the light source corresponding to the time-dependent change amount of the light intensity of the light source; and a shading compensation unit operable to perform shading compensation, when a plurality of document sheets are successively read, such that in advance of reading the first document sheet, the white reference plate is read to acquire light intensity reference data indicative of the light intensities detected by the light sensing elements of the image sensor respectively, and the auxiliary white reference plate is read to acquire light intensity auxiliary reference data indicative of a representative light intensity of the light source, that after reading the first document sheet, the shading compensation is performed to the read data of the first document by the use of the light intensity reference data, that in advance of reading the second or subsequent document sheet, the auxiliary white reference plate is read to acquire latest light intensity auxiliary data indicative of the representative light intensity of the light source, and that after reading the second or subsequent document sheet, the shading compensation is performed to the read data of the second or subsequent document by calculating correction values on the basis of the differential profile data and the ratio of the difference between the light intensity auxiliary reference data and the latest light intensity auxiliary data to the differential profile auxiliary data, and correcting the light intensity reference data with the correction values.

By this configuration, when the first document sheet is read, the light intensity reference data is acquired as well as the light intensity reference auxiliary data which is reference data indicative of the light intensity of the light source lamp obtained by sampling the auxiliary white reference plate. Then, just before reading the second or subsequent document sheet, the auxiliary white reference plate is sampled to acquire the latest light intensity auxiliary data which is the light intensity of the light source lamp, followed by calculating the change amount from the light intensity reference auxiliary data. The change amount is used to correct the light intensity reference data obtained when the first document sheet is read, followed by performing the shading compensation with the corrected light intensity reference data.

In this case, the light intensity reference data is compensated separately for each picture element by referring to the profile data in which is stored the change amount of the sample value of each picture element corresponding to the change amount of the light intensity. As has been discussed above, since the light intensity reference data is compensated separately for each picture element by referring to the profile data, it is possible to perform shading compensation in correspondence with the actual light intensity reduction.

The shading compensation is performed to the read data D of each picture element of a document sheet as corrected read data Ds by the use of a black reference value and the number of gradation levels for representing the read data on the basis of a compensation equation as follows $$Ds = \frac{(D - \text{black reference value}) \times \text{number of gradation levels}}{\left(\begin{array}{c}\text{light intensity reference data} - \\ \text{correction value} - \text{black reference value}\end{array}\right)}.$$

Preferably, the shading compensation is performed separately for each of RGB channels.

On the other hand, in a preferred embodiment, the representative light intensity obtained by reading the auxiliary white reference plate is the average value of the light intensities on the auxiliary white reference plate detected by the light sensing elements of the image sensor.

More specifically speaking, in this case, the average value of the light intensities can be the average value of the light intensities on the auxiliary white reference plate detected by the light sensing elements within a predetermined area having widths both in the main scanning direction and in the secondary scanning direction.

Also, in a preferred embodiment, when a predetermined condition is satisfied, the shading compensation unit updates the differential profile data and the differential profile auxiliary data by the use of the light intensity reference data which is recently acquired and the light intensity auxiliary reference data which is recently acquired.

In this case, just after updating the differential profile data and the differential profile auxiliary data, the shading compensation unit performs shading compensation by the use of the light intensity reference data which is recently acquired even for the second or subsequent document sheet.

Meanwhile, the predetermined condition may be the condition that a predetermined number of document sheets have been read, that a predetermined time elapses after starting the image reading process, or that the difference between the light intensity auxiliary reference data and the latest light intensity auxiliary data has exceeded the differential profile auxiliary data.

Also, when the white reference plate is read, the white reference plate is scanned along a plurality of lines in the secondary scanning direction, and the average value of the light intensities detected by the light sensing elements along each of the plurality of lines in the secondary scanning direction is used as the light intensity detected by the light sensing elements of the image sensor respectively.

Furthermore, in a preferred embodiment, the differential profile data is calculated by detecting the change amounts of the light intensity on the white reference plate detected by the light sensing elements, and averaging the change amounts in the main scanning direction.

In accordance with a second aspect of the present invention, an image reading method is provided for an image reading apparatus which is provided with a light source and an image sensor having a plurality of light sensing elements arranged in the main scanning direction, and operable to irradiate an object to be read with light emitted from the light source and read the reflected light from the object by the image sensor. The image reading method comprises: a step of storing differential profile data indicative of a time-dependent change amount of the light intensity of a white reference plate, which has a length which is no shorter than the main scanning width of the image sensor, detected by each of the light sensing elements corresponding to a time-dependent change amount of the light intensity of the light source, and differential profile auxiliary data indicative of a time-dependent change amount of a light intensity on the auxiliary white reference plate, which is smaller than the white reference plate, read by the image sensor as a representative light intensity of the light source corresponding to the time-dependent change amount of the light intensity of the light source; and a step of performing shading compensation, when a plurality of document sheets are successively read, such that in advance of reading the first document sheet, the white reference plate is read to acquire light intensity reference data indicative of the light intensities detected by the light sensing elements of the image sensor respectively, and the auxiliary white reference plate is read to acquire light intensity auxiliary reference data indicative of a representative light intensity of the light source, that after reading the first document sheet, the shading compensation is performed to the read data of the first document by the use of the light intensity reference data, that in advance of reading the second or subsequent document sheet, the auxiliary white reference plate is read to acquire latest light intensity auxiliary data indicative of the representative light intensity of the light source, and that after reading the second or subsequent document sheet, the shading compensation is performed to the read data of the second or subsequent document by calculating correction values on the basis of the differential profile data and the ratio of the difference between the light intensity auxiliary reference data and the latest light intensity auxiliary data to the differential profile auxiliary data, and correcting the light intensity reference data with the correction values.

As has been discussed above, in accordance with the present invention, it is possible to perform shading compensation in correspondence with the actual light intensity reduction of the light source lamp when correcting the sample values of the white reference plate to compensate the intensity reduction.

BRIEF DESCRIPTION OF THE DRAWINGS

The objects and features of the present invention will become more apparent from consideration of the following detailed description taken in conjunction with the accompanying drawings in which.

DESCRIPTION OF THE PREFERRED EMBODIMENTS

In what follows, an embodiment of the present invention will be explained in conjunction with the accompanying drawings.

In accordance with the image reading apparatus of the present embodiment, an image reading process can be selectively performed either in a sheet-through reading mode in which images are successively read by automatically picking up one after another a plurality of document sheets stacked on an automatic reading document tray, or in a flatbed reading mode in which images are captured from document sheets which are manually placed one after another on a document reading area by the user. In the sheet-through reading mode, the image reading process is performed by fixing a carriage which carries a light source lamp for irradiating a document sheet with light and a mirror for receiving a reflected light from the document sheet, and automatically transporting the document sheet. Contrary to this, in the flatbed reading mode, the image reading process is performed by fixing a document sheet and moving the carriage to scan the document sheet.

On the other hand, the shading compensation to be performed in advance of capturing an image of a document sheet is performed either as an ordinary shading compensation which is performed by sampling a black reference value and a white reference value for each picture element in advance of reading the document sheet, or as a simplified shading compensation which is performed by detecting the variation of the light intensity of the light source lamp.

Figure 1A:
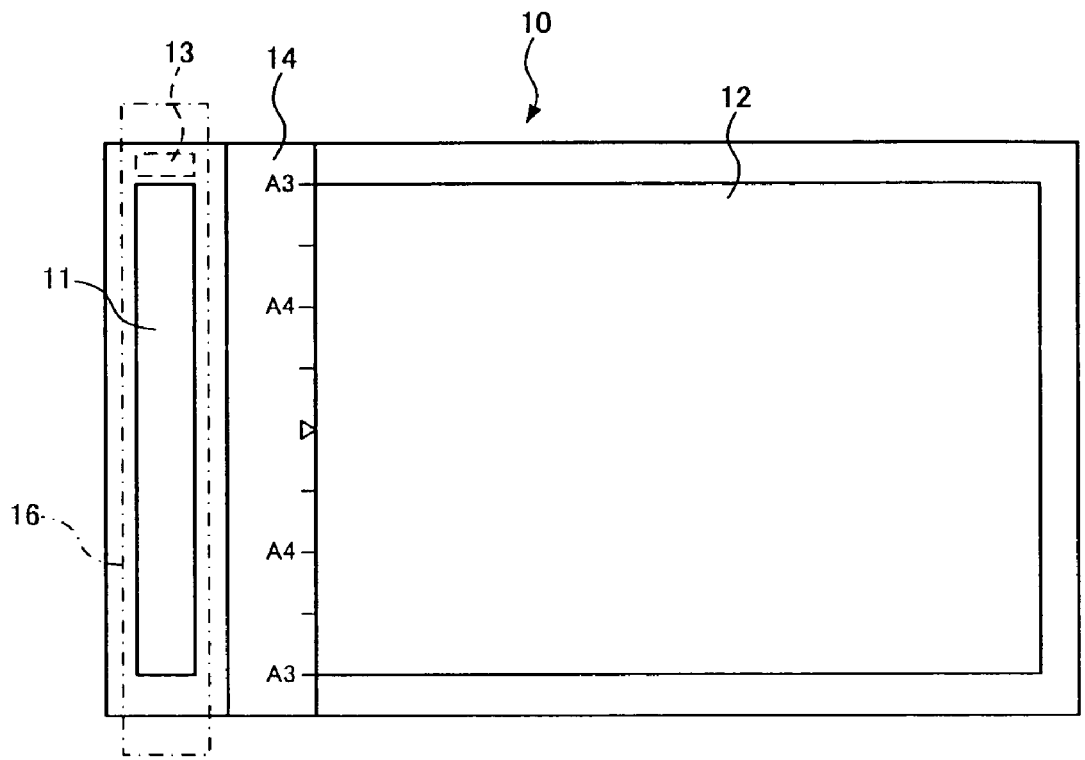
FIG. 1A is a plan view for schematically showing the configuration of the image reading plane of an image reading apparatus in accordance with the present embodiment.
Figure 1B:
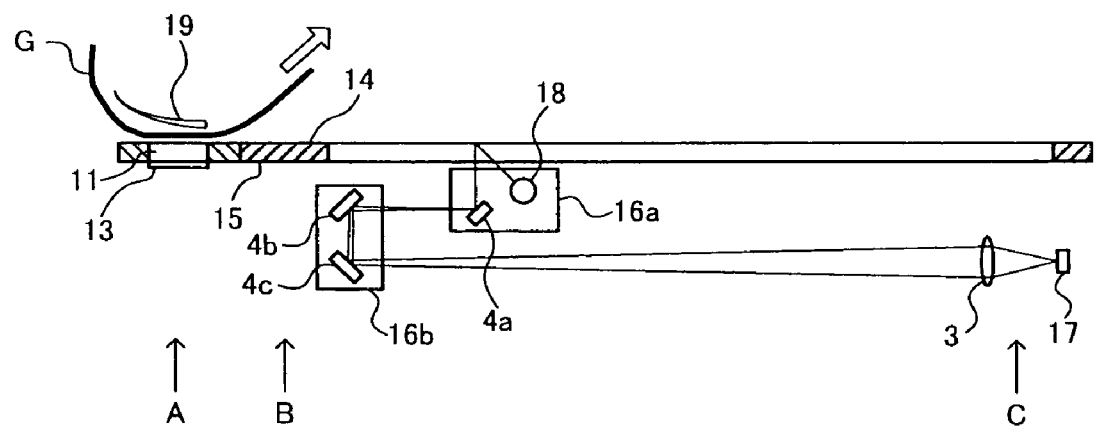
FIG. 1B is a side view for schematically showing the image reading mechanism of the image reading apparatus in accordance with the present embodiment.

FIG. 1A is a plan view for schematically showing the configuration of the image reading plane of an image reading apparatus in accordance with the present embodiment. FIG. 1B is a side view for showing the image reading mechanism of the same apparatus. As shown in FIG. 1A, the image reading apparatus 10 is provided with an automatic reading area 11 providing a document reading plane in which a document sheet can be read in the sheet-through reading mode, and a document set-up area 12 providing a document reading plane in which a document sheet can be read in the flatbed reading mode. These document reading planes are defined by glass plates respectively, and provided with light blocking members surrounding the document reading planes respectively. As shown in FIG. 1B, there is a guide plate 19 above the automatic reading area 11 in order to guide the transportation of a document sheet in the sheet-through reading mode.

Also, there is a position guide plate 14 between the automatic reading area 11 and the document set-up area 12 in order to guide a document sheet in an alignment position when the document sheet is placed thereon in the flatbed reading mode. The position guide plate 14 is provided with markers showing the positions with which document sheets of A3, A4 and the other sizes can be aligned, the center position and so forth on the upper surface thereof, and provided with a white reference plate 15 on the rear surface thereof.

The white reference plate 15 is read to acquire white reference values for ordinary shading compensation. The length of the white reference plate 15 is no smaller than the width of a first mirror 4a which is mounted on a lamp carriage 16a, i.e., no smaller than the readable width for the purpose of generating compensation data for each picture element in the ordinary shading compensation. Incidentally, in the case of the present embodiment, white reference values are sampled by reading the white reference plate 15 when the light source lamp is turned on, and black reference values are sampled by reading the white reference plate 15 when the light source lamp is turned off. However, it is possible to sample black reference values by reading a black reference plate which is additionally provided, or reading another location. Meanwhile, in what follows, the process of sampling black reference values is not specifically described since the present embodiment relates mainly to handling white reference values.

The light radiated from the light source lamp 18 is reflected by a document sheet, and then directed to an image sensor 17 by the first mirror 4a, a second mirror 4b, a third mirror 4b and a lens 3. Then, the image sensor 17 is implemented with a number of light sensing elements arranged in the main scanning direction, and receives the light to capture an image of the document sheet.

The lamp carriage 16a carrying the light source lamp 18 and the first mirror 4a is fixed to a position A corresponding to the automatic reading area 11 in the sheet-through reading mode, and is used to capture an image of a document sheet G which is transported by an automatic document transportation mechanism (not shown in the figure). On the other hand, in the flatbed reading mode, the lamp carriage 16a performs ordinary shading compensation by sampling white reference values in a position B corresponding to the white reference plate 15, and then moves toward an end position C of the document set-up area 12 by a carriage transportation mechanism (not shown in the figure) in order to capture an image of a document sheet which is placed on the document set-up area 12.

The second mirror 4b and the third mirror 4c are carried on a mirror carriage 16b which is moved in synchronization with the motion of the lamp carriage 16a by a motion amount which is half the motion amount of the lamp carriage 16a. The image reading apparatus 10 of the present embodiment employs a so-called full/half rate mirror scan method which makes constant, during scanning, the distance between the read surface of a document sheet and the image sensor 17 which is fixed to the housing.

An auxiliary white reference plate 13 is provided on the rear surface of the light blocking member located on the main scanning direction side of the automatic reading area 11. The auxiliary white reference plate 13 is provided for the purpose of detecting the variation of the light intensity of the light source lamp. The auxiliary white reference plate 13 is located in such a position that it can be read by the lamp carriage 16*a* which is fixed to the position A corresponding to the automatic reading area 11. Since the auxiliary white reference plate 13 is used only to measure the light intensity of the light source lamp 18, the auxiliary white reference plate 13 can be smaller than the white reference plate 15. Incidentally, the auxiliary white reference plate 13 is a white plate having a uniform reflectance (for example, a white mylar sheet) as well as the white reference plate 15. However, the auxiliary white reference plate 13 can be replaced by another member or provided in another location.

Figure 2:
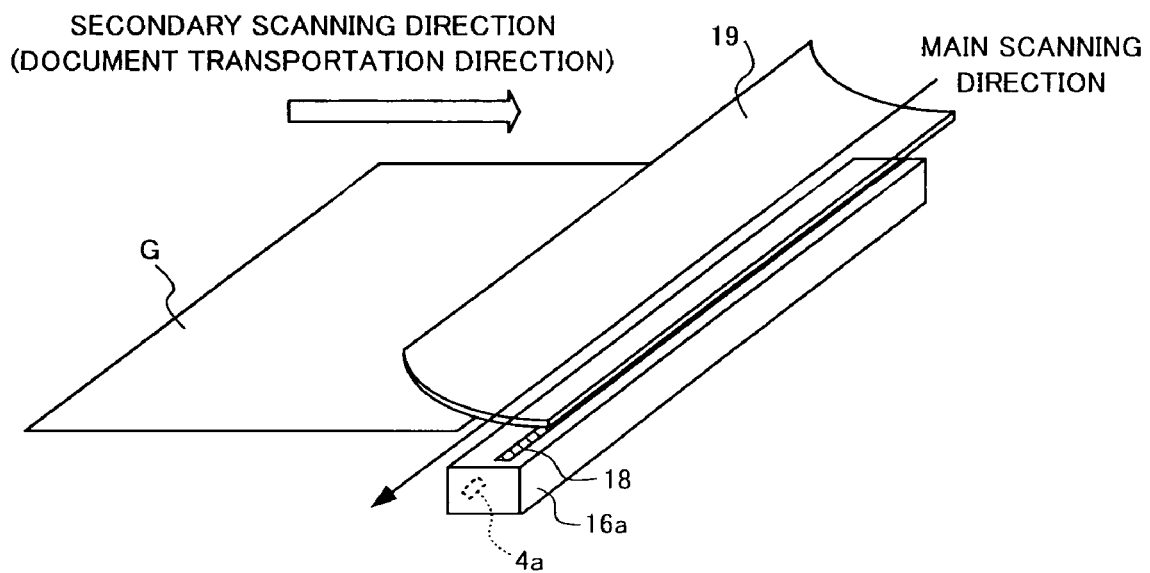
FIG. 2 is a perspective view for showing the lamp carriage which is located in the position corresponding to the automatic reading area of the image reading apparatus in accordance with the present embodiment.

FIG. 2 is a perspective view for showing the lamp carriage 16*a* which is located in the position A corresponding to the automatic reading area 11. As shown in the same figure, the lamp carriage 16*a* is provided with the light source lamp 18 such as a cold-cathode tube and the first mirror 4*a* in order to reflect the light, which is radiated from the light source lamp 18, by the surface of the object to be read by the first mirror 4*a*, and direct the reflected light to the second mirror 4*b* of the mirror carriage 16*b*. However, it is possible to mount a line image sensor on the lamp carriage 16*a* to implement a so-called contact type structure in which the reflected light from a document sheet is directly read by the line image sensor.

In the sheet-through reading mode, the document sheet G is guided and transported to the guide plate 19 by an automatic document transportation mechanism (not shown in the figure) in the direction (the secondary scanning direction) perpendicular to the direction of moving the lamp carriage 16*a* (the main scanning direction) in order to capture an image on a line-by-line basis.

Figure 3:
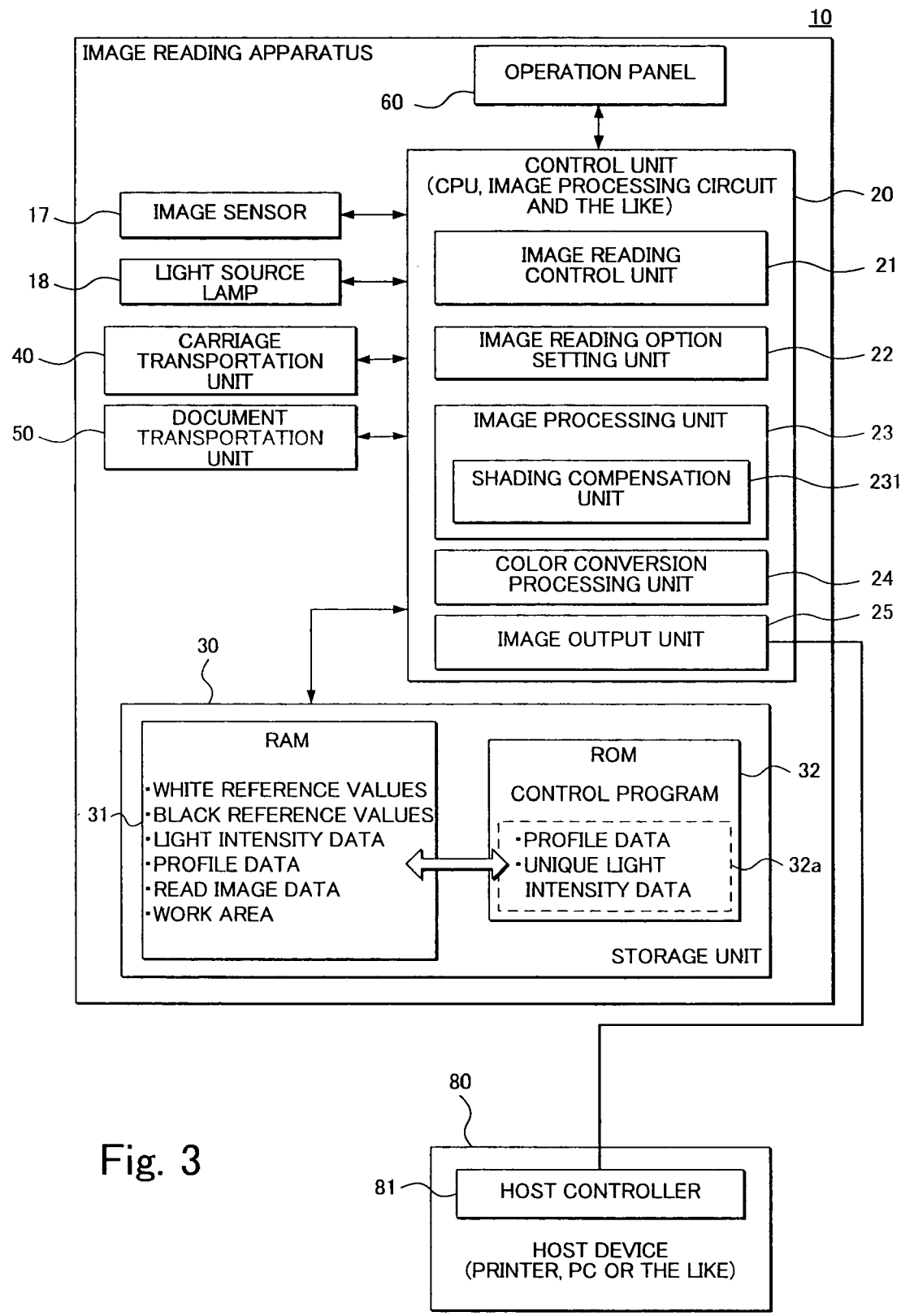
FIG. 3 is a block diagram for showing the functional configuration of the image reading apparatus and the control system of a host device which receives image data from the image reading apparatus in accordance with the present embodiment.

FIG. 3 is a block diagram for showing the functional configuration of the image reading apparatus 10 and the control system of a host device 80 which receives image data from the image reading apparatus 10. As shown in the same figure, the image reading apparatus 10 is provided with a control unit 20, a storage unit 30, a carriage transportation unit 40, a document transportation unit 50, and an operation panel 60 in addition to the image sensor 17 and the light source lamp 18 as described above. However, the operation panel 60 can be provided external to the image reading apparatus 10, for example, provided on the host device 80 side.

The control unit 20 includes a CPU, an image processing circuit, an interface circuit and so forth, and controls the image reading process of the image reading apparatus 10. In the case of the present embodiment, the control unit 20 is provided with an image reading control unit 21, an image reading option setting unit 22, an image processing unit 23, a color conversion processing unit 24, and an image output unit 25. These units are implemented by having the CPU run a control program which is stored in a ROM 32 to be described below.

The image reading control unit 21 controls the carriage transportation unit 40, the document transportation unit 50 and the light source lamp 18 in accordance with an image reading option accepted by the image reading option setting unit 22 in order to perform the process of reading a document. That is, in the sheet-through reading mode, the process of reading a document sheet is performed by moving the lamp carriage 16*a* to the position corresponding to the automatic reading area 11, and transporting the document sheet by the document transportation unit 50. On the other hand, in the flatbed reading mode, the process of reading a document sheet is performed by moving the lamp carriage 16*a* in the secondary scanning direction with a document sheet which is set up on the document set-up area 12.

The image reading option setting unit 22 accepts the settings of image reading options from the operation panel 60, the host device 80 connected to the image reading apparatus 10, or the like. The image reading options accepted by the image reading option setting unit 22 include, for example, the settings of sheet-through reading mode/flatbed reading mode, double-side/single-side, enlargement/reduction, color/monochrome, the number of gradation levels, resolution and so forth.

The image processing unit 23 performs the process of processing the image data which is read by the image sensor 17. The image processing process includes shading compensation for compensating variations in the sensitivity among the light sensing elements of the image sensor 17. For this purpose, the image processing unit 23 is provided with a shading compensation unit 231 for performing a shading compensation process.

The shading compensation unit 231 can selectively perform either the ordinary shading compensation or the simplified shading compensation as has been discussed above. The ordinary shading compensation is performed by the following steps. That is, in advance of reading the image of a document sheet, white reference values are acquired by sampling the white reference plate 15 with each of the picture elements of the image sensor 17 while the light source lamp 18 is turned on. Then, while the light source lamp 18 is turned on, the process of reading the document sheet is started. The image data as read is compensated by the use of the acquired white reference values and the black reference values which are acquired separately.

The image data value D which is actually read for each picture element can be compensated as a compensated image data value Ds by the use of the white reference value W and the black reference value B in accordance with the following equation.

$$Ds=(D-B)\times \text{the number of gradation levels}/(W-B)$$

Incidentally, it is preferred to perform the shading compensation separately for each of RGB channels in order to improve the accuracy of compensation.

Also, the simplified shading compensation is performed as described below. In this example, the simplified shading compensation is performed for the second and subsequent document sheets, whereas the ordinary shading compensation is performed for the first document sheet. However, it is possible to perform the ordinary shading compensation also for the second or subsequent document sheets when necessary or appropriate.

When performing the simplified shading compensation, the reference value of the light intensity of the light source lamp 18 is sampled from the auxiliary white reference plate 13 when the ordinary shading compensation is performed for the first document sheet. Then, the differential light intensity of the light source lamp 18 from the reference value is calculated by sampling the auxiliary white reference plate 13 just before reading each of the second and subsequent document sheets to acquire the light intensity of the light source lamp 18. The differential light intensity is used to perform the shading compensation by compensating the white reference values acquired when the ordinary shading compensation is performed for the first document sheet. At this time, the white reference value of each picture element is compensated with reference to profile data in which is recorded the differential sample value from the white reference value for each picture element in correspondence with the variations in the light intensity. The simplified shading compensation will be described below in detail.

The color conversion processing unit 24 performs the process of converting RGB image data into CMYK image data, the process of reducing gradation levels, and so forth. The image output unit 25 performs the process of transferring the read image data to the host device 80.

The storing unit 30 is provided with a RAM 30 and a ROM 32. The ROM 32 includes an EEPROM 32a which can be rewritten. The RAM 30 which is a volatile memory is used to store the white reference values which is obtained by sampling the white reference plate 15 and the black reference values, the light intensity data which is obtained by sampling the auxiliary white reference plate 13, the image data which is obtained by reading a document, and so forth. The RAM 30 is used also to provide a work area.

The ROM 32 which is a nonvolatile memory is used to store a control program. The EEPROM 32a which can be rewritten is used to store the profile data, unique light intensity data and so forth which will be described below in detail. The above data is transferred to the RAM 30 for use when starting the operation of the image reading apparatus 10. When the profile data is updated, it is written back to the EEPROM 32a.

The carriage transportation unit 40 can be implemented with a motor, a drive belt and the like, and moves the lamp carriage 16a to the reading position or moves the lamp carriage 16a in the secondary scanning direction under the control of the image reading control unit 21. The carriage transportation unit 40 also moves the mirror carriage 16b in synchronization with the motion of the lamp carriage 16a by a motion amount which is half the motion amount of the lamp carriage 16a. The document transportation unit 50 includes a document reversion mechanism which reverses a document sheet for reading the back side thereof after reading the main side thereof if double-side reading is designated as a reading option.

The host device 80 is for example a printer, a PC or the like, and provided with a host controller 81 which is connected to the image reading apparatus and controls the process of receiving image data.

Figure 4:
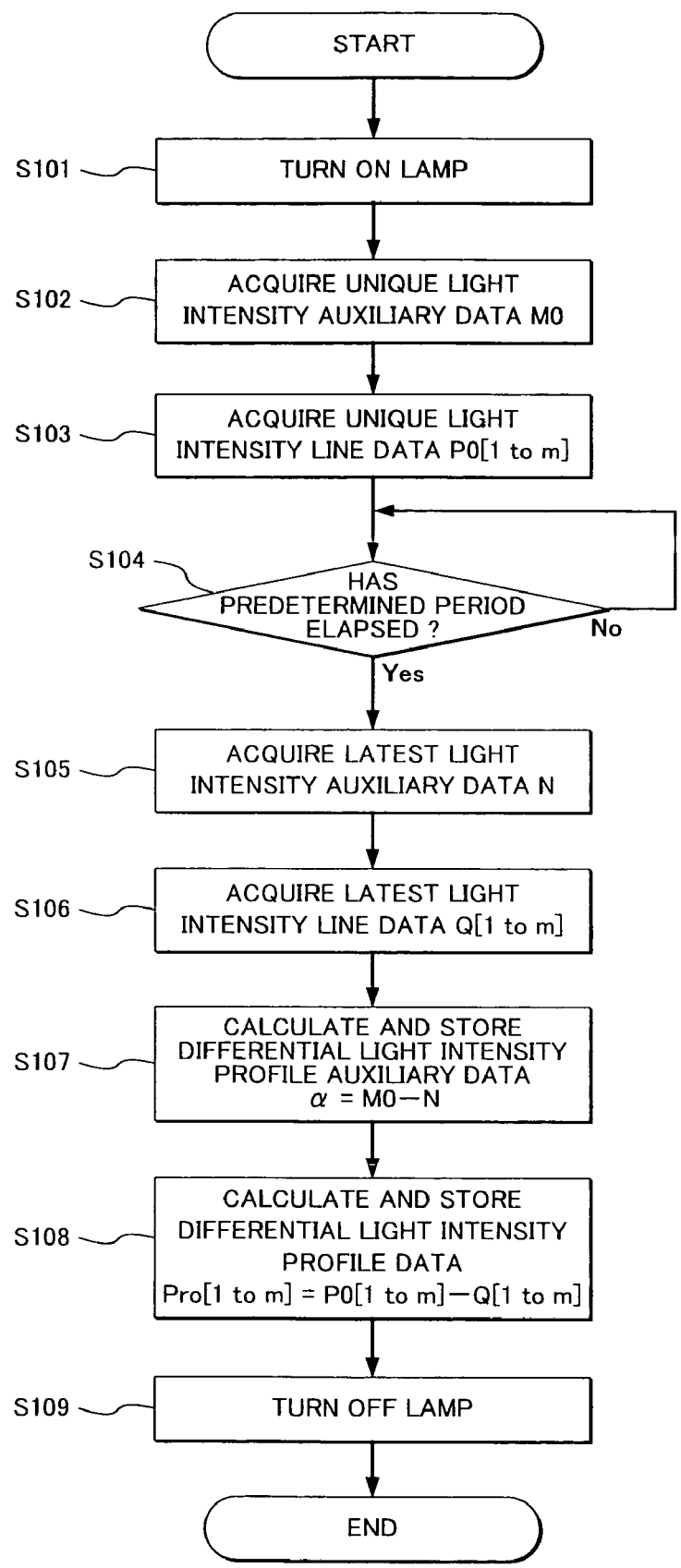
FIG. 4 is a flow chart for showing the process of acquiring unique light intensity line data P0[1 to m] and unique light intensity auxiliary data M0 of the image reading apparatus 10, and the process of acquiring the initial values of differential light intensity profile data Pro[1 to m] and the initial values of differential light intensity profile auxiliary data α in accordance with the present embodiment.

Next is an explanation of the characteristic process performed by the image reading apparatus 10 having the structure as described above with reference to several flow charts. FIG. 4 is a flow chart for showing the process of acquiring unique light intensity line data P0[1 to m] and unique light intensity auxiliary data M0 of the image reading apparatus 10, and the process of acquiring the initial values of differential light intensity profile data Pro[1 to m] and the initial values of differential light intensity profile auxiliary data α.

In this case, the unique light intensity line data P0[1 to m] contains a value which is sampled from the white reference plate 15 for each picture element just after turning on the light source lamp 18 without a light intensity loss. Meanwhile, the value "m" is typically the number of the picture elements of the image sensor 17 which are used to read images. The unique light intensity auxiliary data M0 contains a representative value which is obtained by sampling the auxiliary white reference plate 13 just after turning on the light source lamp 18 without a light intensity loss. In the case of the present embodiment, the light intensity auxiliary data is used to represent the light intensity of the light source lamp 18 so that it uses the representative value of sample values rather than values provided separately for the picture elements respectively.

The representative value can for example be the average value of the values which are sampled with a plurality of picture elements when reading the auxiliary white reference plate 13. It is thereby possible to reduce the influence of dirt, unevenness or the like of the auxiliary white reference plate 13. The plurality of picture elements may be the picture elements located within an area defined by the predetermined length in the main scanning direction and the predetermined length in the secondary scanning direction. Alternatively, the representative value may be calculated as the average value of a plurality of picture elements only along the main scanning direction.

The unique light intensity line data P0[1 to m] and the unique light intensity auxiliary data M0 are stored in the EEPROM 32a as information unique to the image reading apparatus 10. Preferably, the above process of storing the unique information is performed, for example, in advance of shipping the image reading apparatus 10, or when installing the image reading apparatus 10 for use. Alternatively, the above process of storing the information unique may be performed when the image reading apparatus 10 is inspected.

Also, the differential light intensity profile data Pro[1 to m] is the data calculated by reading the white reference plate 15 after the light source lamp 18 is turned on for a period, and includes a value for each picture element indicative of how much the sample value is diminished due to a light intensity loss. The differential light intensity profile auxiliary data α is the data calculated by reading the auxiliary white reference plate 13 after the light source lamp 18 is turned on for a period, and is the data indicative of how much the light intensity of the light source lamp 18 is diminished.

As has been discussed above, in the case of the present embodiment, the differential light intensity profile data Pro[1 to m] and the differential light intensity profile auxiliary data α are used to associate the differential sample values of the white reference plate 15 with the differential light intensity of the light source lamp 18 between when the operation of the image reading apparatus 10 is started and when a predetermined time elapses after the light source lamp 18 is turned on. Then, when performing the simplified shading compensation during an actual scanning job, the differential sample value of the white reference plate 15 for each picture element is estimated only by acquiring the differential sample value of the auxiliary white reference plate 13 with reference to the profile data.

The initial values of the differential light intensity profile data Pro[1 to m] and differential light intensity profile auxiliary data α are calculated by this process and stored in the EEPROM 32a. These values are updated if necessary when the user uses the image reading apparatus 10 for image reading process.

As shown in FIG. 4, this process is started by turning on the light source lamp 18 in step S101. Then, before the light intensity diminishes, the unique light intensity auxiliary data M0 is acquired in step S102. Since the unique light intensity auxiliary data M0 is acquired by sampling the auxiliary white reference plate 13, the lamp carriage 16a is moved to the position corresponding to the automatic reading area 11 in advance. The predetermined area of the auxiliary white reference plate 13 is sampled followed by calculating the average value of the read sample values to acquire the unique light intensity auxiliary data M0. The predetermined area may, for example, be a rectangular area of X picture elements in the main scanning direction and X picture elements in the secondary scanning direction.

Next, the unique light intensity line data P0[1 to m] is acquired in step S103. Since the unique light intensity line data P0[1 to m] is acquired by sampling the white reference plate 15, the lamp carriage 16a is moved to the position corresponding to the white reference plate 15. The unique light intensity line data P0[1 to m] is then acquired by sampling the white reference plate 15 along a plurality of lines, and averaging the sample values detected by each picture element to obtain the unique light intensity line data P0[1 to m]. In this manner, by averaging the sample values in the secondary scanning direction, it is possible to reduce the influence of dirt, unevenness or the like of the white reference plate 15. However, the white reference plate 15 can be sampled along only one line. Also, it is possible to change the order of acquiring the unique light intensity auxiliary data M0 and the unique light intensity line data P0[1 to m]. The acquired unique light intensity auxiliary data M0 and unique light intensity line data P0[1 to m] are stored in the EEPROM 32a, followed by waiting for a predetermined period to elapse in step S104 for acquiring data after the light intensity of the light source lamp 18 has substantially diminished. The predetermined time is, for example, 10 minutes.

After the predetermined time has elapsed ("Yes" in step S104), the latest light intensity auxiliary data N is acquired in step S105. The latest light intensity auxiliary data N is the value which is a representative value of the most recent sample values of the auxiliary white reference plate 13 after the light intensity has diminished. The process of sampling the auxiliary white reference plate 13 and the method of calculating the representative value are equivalent to those of the acquired unique light intensity auxiliary data M0.

Furthermore, the latest light intensity line data Q[1 to m] is acquired in step S106. The latest light intensity line data Q[1 to m] contains the most recent value of each picture element when sampling the white reference plate 15 after the light intensity has diminished. The method of reading the white reference plate 15 is equivalent to that of the unique light intensity line data P0[1 to m] . It is possible to change the order of acquiring the latest light intensity auxiliary data N and the latest light intensity line data Q[1 to m].

Next, the differential light intensity profile auxiliary data α is calculated and stored in the EEPROM 32a in step S107. The differential light intensity profile auxiliary data α is calculated by subtracting the latest light intensity auxiliary data N from the acquired unique light intensity auxiliary data M0. Namely, the differential light intensity profile auxiliary data α contains the differential light intensity between the light intensities of the light source lamp 18 before and after the light intensity has diminished.

The differential light intensity profile data Pro[1 to m] is calculated by subtracting the latest light intensity line data Q[1 to m] from the unique light intensity line data P0[1 to m], and stored in the EEPROM 32a in step S108. Namely, the differential light intensity profile data Pro[1 to m] contains the differential sample value of the white reference plate 15 for each picture element between the light intensities of the light source lamp 18 before and after the light intensity has diminished.

When the above process is completed, the light source lamp 18 is turned off followed by finishing the process of acquiring the unique light intensity line data P0[1 to m], the process of acquiring the unique light intensity auxiliary data M0, and the process of acquiring the initial data of the differential light intensity profile data Pro[1 to m] and the initial data of the differential light intensity profile auxiliary data α.

Figure 5:
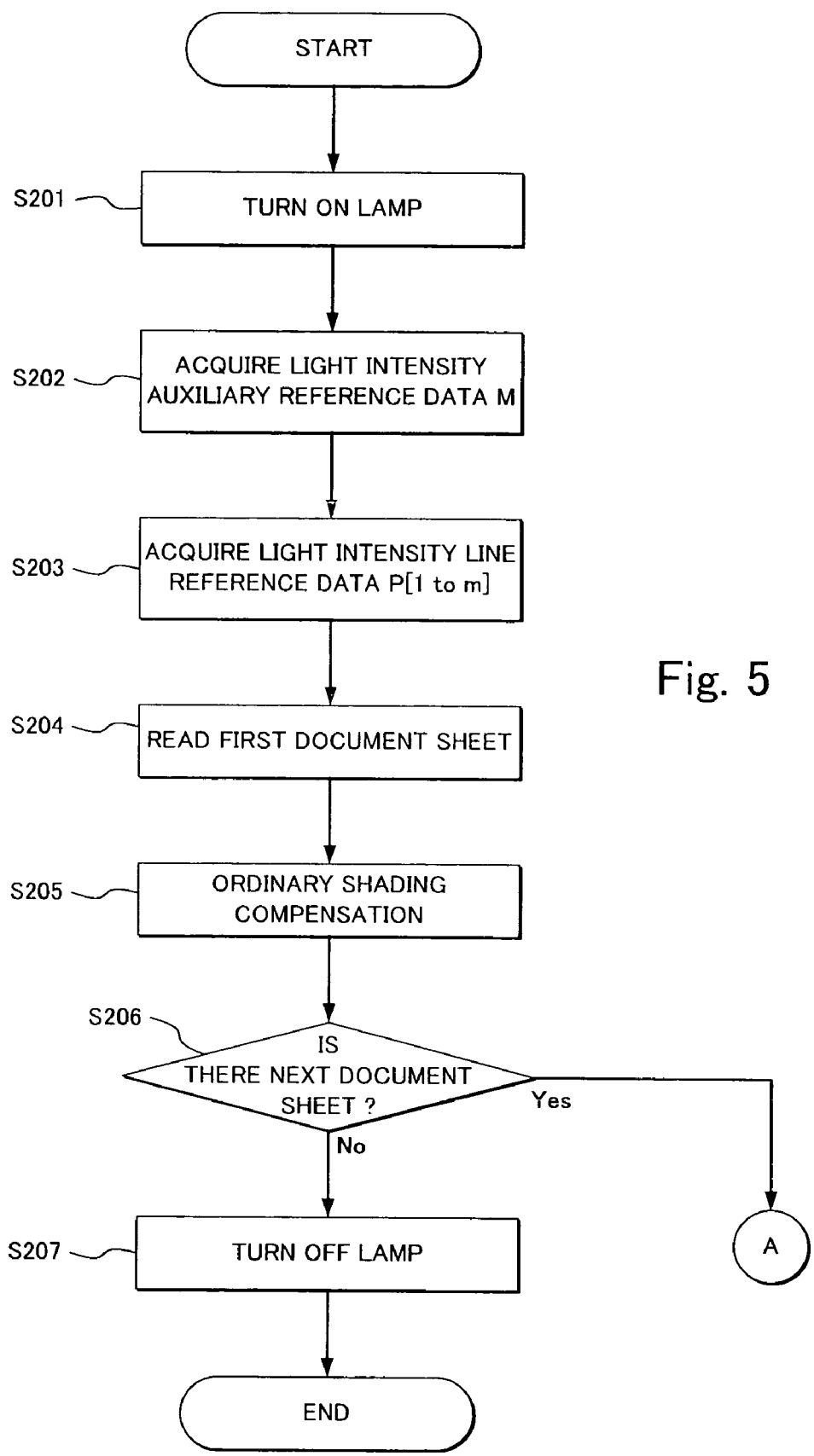
FIG. 5 is a flow chart for showing the process performed by the image processing apparatus when reading the first document sheet in accordance with the present embodiment.
Figure 6:
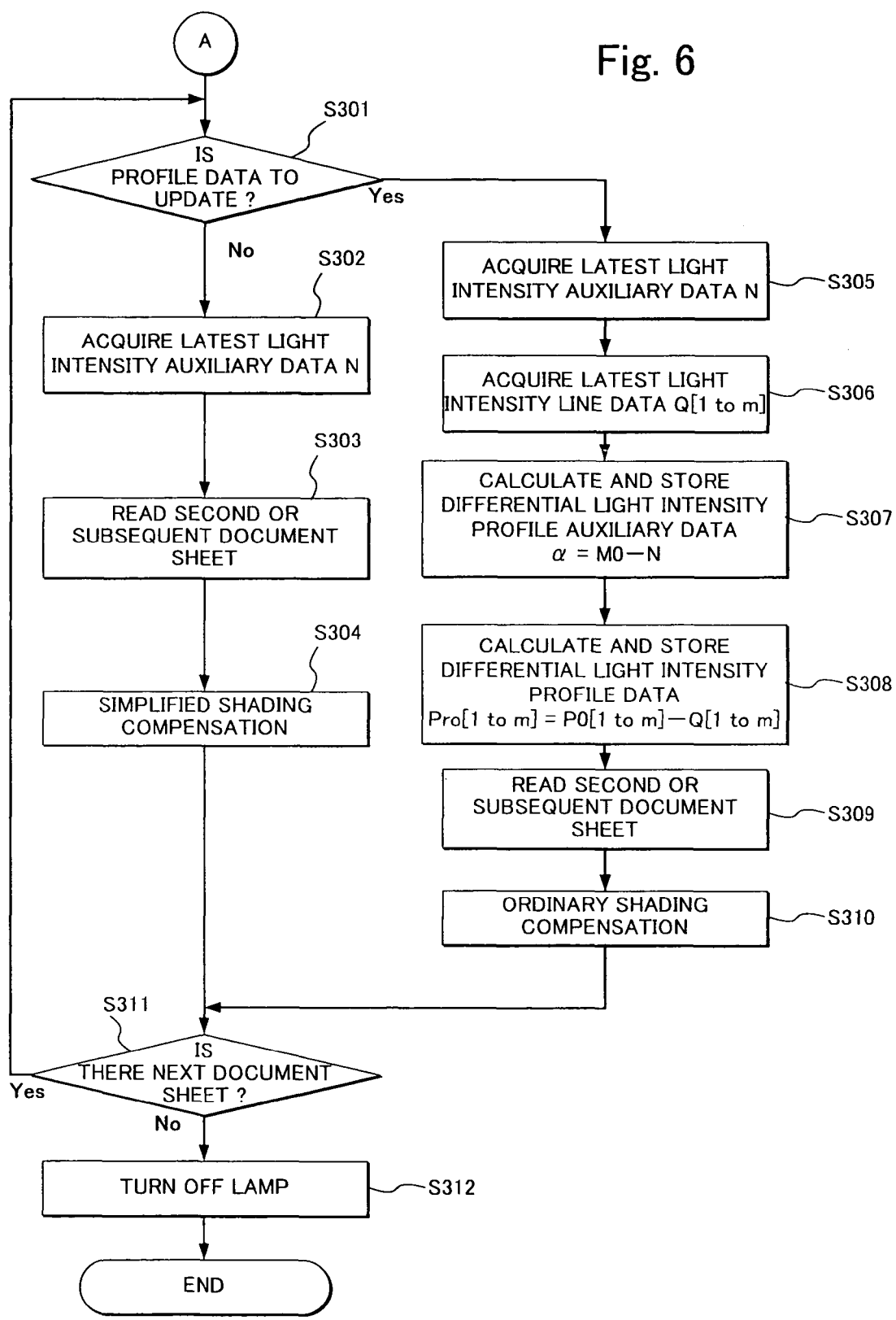
FIG. 6 is a flow chart for showing the process performed by the image processing apparatus when reading the second document sheet in accordance with the present embodiment.

Next, the process performed by the image processing apparatus 10 when reading document sheets will be described with reference to the flow chart shown in FIG. 5 and FIG. 6. When a plurality of document sheets are successively read in the actual reading process, different shading compensation control procedures are used between reading the first document sheet and reading the second and subsequent document sheets.

More specifically speaking, when the first document sheet is read, the ordinary shading compensation is performed, and necessary data is acquired as reference light intensities. On the other hand, when the second and subsequent document sheets are read, the simplified shading compensation is performed. By this scheme, the throughput of reading document sheets can be increased. Meanwhile, it is possible to update the profile data when the second and subsequent document sheets are read, if necessary or appropriate. In this case, the ordinary shading compensation is performed for the subsequent document sheet.

When the image reading process is performed, the user makes the settings of the reading mode and other reading options such as color/monochrome. The present embodiment is particularly effective in the sheet-through reading mode in which images are successively read by automatically picking up one after another a plurality of document sheets from a feeder tray.

The image reading process is started by turning on the light source lamp 18 in step S201. Then, a light intensity auxiliary reference data M is acquired before the light intensity is diminished in step S202. This light intensity auxiliary reference data M is a reference light intensity for use in performing the current image reading job. Since the auxiliary white reference plate 13 is sampled for acquiring the light intensity auxiliary reference data M, the lamp carriage 16a is moved to the position corresponding to the automatic reading area 11. Then, the predetermined area of the auxiliary white reference plate 13 is sampled to calculate the average value of the read sample values which is set to the light intensity auxiliary reference data M. The predetermined area for use in acquiring the unique light intensity auxiliary data M0 can be used as the predetermined area for use in acquiring the light intensity auxiliary reference data M.

Next, light intensity line reference data P[1 to m] are acquired in step S203. This light intensity line reference data P[1 to m] is light intensity line reference data for use in performing the current image reading job. Since the white reference plate 15 is sampled for acquiring the light intensity line reference data P[1 to m], the lamp carriage 16a is moved to the position corresponding to the white reference plate 15. Then, the white reference plate 15 is sampled along a plurality of lines, and the sample values detected by each picture element to obtain the light intensity line reference data P[1 to m].

Next, the first document sheet is read in step S204, followed by performing ordinary shading compensation to the read image data of the first document sheet in step S205. The ordinary shading compensation is performed by the use of the light intensity line reference data P[1 to m] as the white reference values in accordance with the above equation.

If there is no sheet as the next document sheet (i.e., the "No" branch from step S206), the light source lamp 18 is turned off in step S207, and the image reading process is finished. Conversely, if there is a next document sheet (i.e., the "Yes" branch from step S206), it is determined whether to update the profile data in step S301.

In this case, a variety of determination criteria can be used to determine whether to update the profile data. For example, the profile data may be updated each time after a predetermined number of document sheets are read. Alternatively, the profile data may be updated if it is determined, as a result of acquiring the latest light intensity auxiliary data N which is described below, that the light intensity of the light source lamp 18 decreases by an amount exceeding a predetermined value, for example, the differential light intensity profile auxiliary data a. Furthermore, the profile data may be updated after the image reading process is continued for a predetermined time.

Generally speaking, the reduction of the light intensity of the light source lamp 18 depends upon the environmental temperature. Accordingly, in order to improve the accuracy of shading compensation in correspondence with the actual light intensity reduction, it is preferred to update the profile data in accordance with the environment when the image reading process is performed.

The accuracy of the shading compensation can be improved by updating the profile data. When the profile data is updated, the latest light intensity line data Q[1 to m] has to be acquired to be described below. However, the latest light intensity line data Q[1 to m] is acquired only after moving the lamp carriage 16a to the position corresponding to the white reference plate 15, and thereby the productivity of the reading process tends to be decreased.

In this situation, it is possible to provide a high productivity mode and a high image quality mode such that the profile data is more frequently updated when the user selects the high image quality mode. Conversely, it is also possible not to compromise the productivity by updating only after completing the image reading job.

If it is determined that the profile data is not updated (i.e., the "No" branch from step S301), the latest light intensity auxiliary data N is acquired in advance of reading a document sheet for the purpose of detecting the current light intensity of the light source lamp 18 in step S302. When the latest light intensity auxiliary data N is acquired, the predetermined area of the auxiliary white reference plate 13 is sampled followed by calculating the average value of the read sample values to acquire the latest light intensity auxiliary data N. In the sheet-through reading mode, the auxiliary white reference plate 13 can be sampled without need for moving the lamp carriage 16a.

Then, the image of a document sheet is captured in step S303 followed by performing the simplified shading compensation to the captured image data in step S304.

Figure 7:
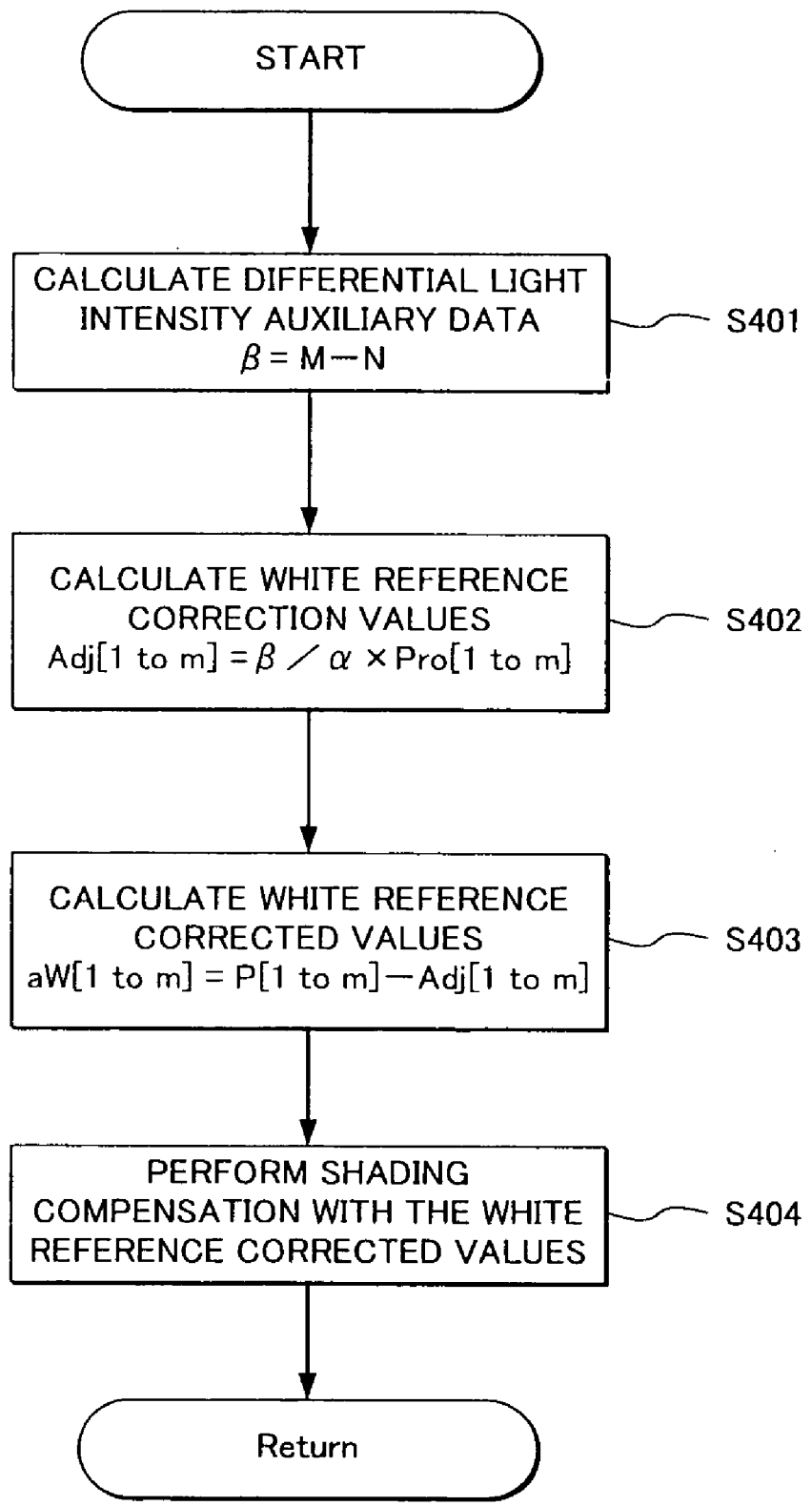
FIG. 7 is a flow chart for showing the steps of the simplified shading compensation in accordance with the present embodiment.

FIG. 7 is a flow chart for showing the steps of the simplified shading compensation. As shown in the same figure, in the simplified shading compensation, differential light intensity auxiliary data β is calculated in step S401 by subtracting the latest light intensity auxiliary data N, which is most recently acquired, from the light intensity auxiliary reference data M which is acquired in advance of reading the first document sheet. The differential light intensity auxiliary data β indicates the light intensity reduction of the light source lamp 18 at the present time after starting the image reading job.

Next, as shown in the following equation, white reference correction values Adj[1 to m] for the respective picture elements are calculated in step S402 by multiplying the differential light intensity profile data Pro[1 to m] and the ratio of the differential light intensity auxiliary data β to the differential light intensity profile auxiliary data α.

$$Adj[1 \text{ to } m] = \beta/\alpha \times Pro[1 \text{ to } m]$$

The white reference correction values Adj[1 to m] are estimated values indicative of how much the light intensity line reference data P[1 to m], which is acquired in advance of reading the first document sheet, is reduced at the position corresponding to each picture element.

Next, white reference corrected values aW[1 to m] are calculated in step S403 by subtracting the white reference correction values Adj[1 to m] from the light intensity line reference data P[1 to m]. The shading compensation is performed by the use of the white reference corrected values aW[1 to m] as white reference values in step S404. The simplified shading compensation is then finished.

After finishing the simplified shading compensation, it is determined whether or not there is another sheet as the next document sheet in step S311. If there is no sheet as the next document sheet (i.e., the "No" branch from step S311), the light source lamp 18 is turned off in step S312, and the image reading process is finished. Conversely, if there is a next document sheet (i.e., the "Yes" branch from step S311), it is determined whether to update the profile data in step S301.

When the profile data is to be updated (i.e., the "Yes" branch from step S301), at first, the latest light intensity auxiliary data N is acquired in order to obtain the current light intensity of the light source lamp 18 in step S305. The latest light intensity auxiliary data N is acquired by sampling the predetermined area of the auxiliary white reference plate 13 and calculate the average value of the read sample values as the latest light intensity auxiliary data N.

Then, the latest light intensity line data Q[1 to m] is acquired in step S306. Since the latest light intensity line data Q[1 to m] is acquired by sampling the white reference plate 15, the lamp carriage 16a is moved to the position corresponding to the white reference plate 15. Then, the white reference plate 15 is sampled along a plurality of lines, and the sample values detected by each picture element to obtain the latest light intensity line data Q[1 to m].

Next, the differential light intensity profile auxiliary data α is calculated and updated in step S307. The differential light intensity profile auxiliary data a is calculated by subtracting the latest light intensity auxiliary data N, which is most recently acquired, from the acquired unique light intensity auxiliary data M0.

On the other hand, the differential light intensity profile data Pro[1 to m] is calculated and updated in step S308. The differential light intensity profile data Pro[1 to m] is calculated by subtracting the latest light intensity line data Q[1 to m], which is most recently acquired, from the unique light intensity line data P0[1 to m]. By this process, the respective profile data is updated.

Thereafter, the image of a document sheet is captured in step S309 followed by performing the ordinary shading compensation to the captured image data in step S310. Namely, since the latest light intensity line data Q[1 to m] has been acquired by the process of updating the profile data, the ordinary shading compensation can be performed by the use of this data.

Then, it is determined whether or not there is another sheet as the next document sheet in step S311. If there is no sheet as the next document sheet (i.e., the "No" branch from step S311), the light source lamp 18 is turned off in step S312, and the image reading process is finished. Conversely, if there is a next document sheet (i.e., the "Yes" branch from step S311), it is determined whether to update the profile data in step S301.

In the case of the above embodiment, the differential light intensity profile data is the differential light intensity line data between the light intensities of the light source lamp 18 before and after the light intensity has diminished. However, the light intensity line data is obtained by sampling the white reference plate 15, and thereby may be affected by noise and dirt of the white reference plate 15. It is possible to reduce the influence of such noise and dirt by sampling the light intensity line data along a plurality of lines and calculating average values thereof. However, since the differential light intensity profile data consists of differential values, even small noise can appear to be reflected in substantial variations.

Furthermore, the differential light intensity profile data is used to represent the influence of the light intensity reduction of the light source lamp 18 on the respective picture elements when performing shading compensation which compensates for characteristic of the respective light sensing elements, and thereby it is preferred that the differential light intensity profile data is roughly indicative of the tendency of light intensity reduction in the main scanning direction.

Therefore, it is possible to apply an averaging procedure in the main scanning direction to the differential light intensity profile data obtained as the differential light intensity line data.

For example, when calculating the value corresponding to each picture element of the differential light intensity profile data, the averaging procedure may be performed by calculating the weighted average value of the differential light intensities of several picture elements in the vicinity of the each picture element. In this case, the differential light intensity profile data can be calculated as Pro_Av[n] by averaging procedure as follows.

$$Pro\_Av[n] = Pro[n-2]/16 + Pro[n-1]/4 + Pro[n]/4 + Pro[n]/8 + Pro[n+1]/4 + Pro[n+2]/16$$

Alternatively, the differential light intensity profile data can be calculated by a 16-elements averaging procedure or an 8-elements averaging procedure as follows.

$$Pro\_Av[n] = Pro[n-4]/8 + Pro[n-3]/8 + Pro[n-2]/8 + Pro[n-1]/8 + Pro[n]/8 + Pro[n+1]/8 + Pro[n+2]/8 + Pro[n+3]/8$$

Furthermore, the differential light intensity profile data can be obtained by performing the above averaging procedure of the light intensity line data both before and after the light intensity has diminished, and then calculating the differential light intensity between the light intensities before and after the light intensity has diminished corresponding to each light sensing element.

Figure 8A:
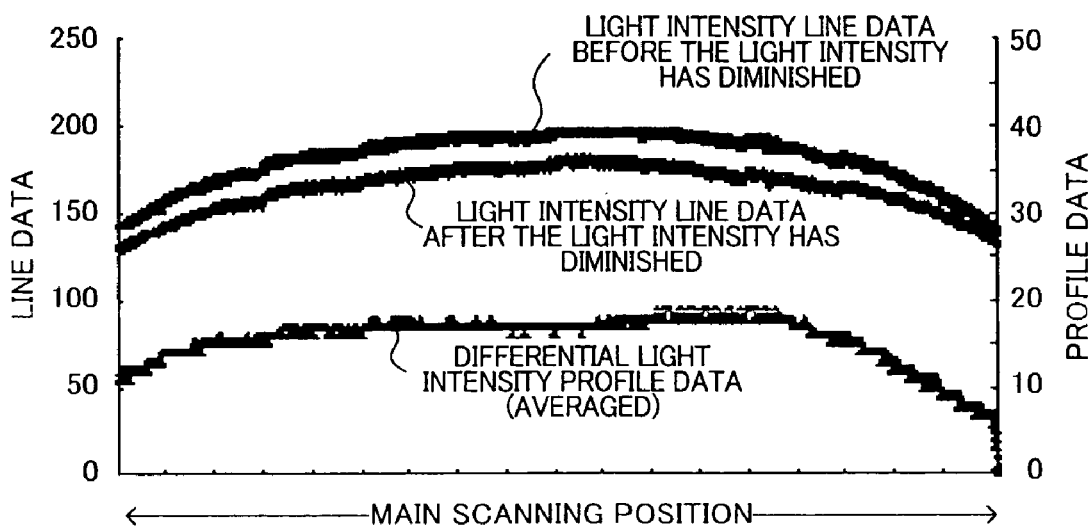
FIG. 8A is a graphic diagram for showing line data before the light intensity has diminished, line data after the light intensity has diminished, and the differential light intensity profile data therebetween after performing the averaging procedure in accordance with the present embodiment.
Figure 8B:
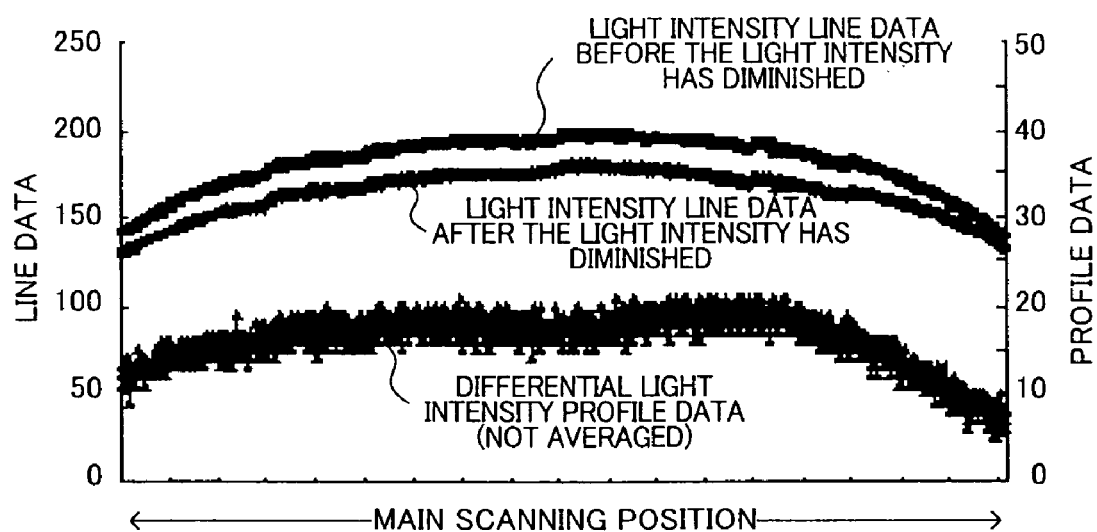
FIG. 8B is a graphic diagram for showing line data before the light intensity has diminished, line data after the light intensity has diminished, and the differential light intensity profile data therebetween without performing the averaging procedure in accordance with the present embodiment.

FIG. 8A is a graphic diagram for showing line data before the light intensity has diminished, line data after the light intensity has diminished, and the differential light intensity profile data therebetween after performing the averaging procedure. On the other hand, FIG. 8B is a graphic diagram for showing line data before the light intensity has diminished, line data after the light intensity has diminished, and the differential light intensity profile data therebetween without performing the averaging procedure. As shown in the same figure, by performing the averaging procedure, it is possible to inhibit the differential light intensity profile data from being affected by the influence of noise and the like, and obtain information about the general tendency of light intensity reduction in the main scanning direction. Meanwhile, because the differential light intensity profile data consists of small values, different dimensions are used between the line data and the profile data in this chart.

The foregoing description of the embodiments has been presented for purposes of illustration and description. It is not intended to be exhaustive or to limit the invention to the precise form described, and obviously many modifications and variations are possible in light of the above teaching. The embodiment was chosen in order to explain most clearly the principles of the invention and its practical application thereby to enable others in the art to utilize most effectively the invention in various embodiments and with various modifications as are suited to the particular use contemplated.

What is claimed is:

1. An image reading apparatus provided with a light source and an image sensor having a plurality of light sensing elements arranged in a main scanning direction, and operable to irradiate an object to be read with light emitted from the light source and read reflected light from the object by the image sensor, the image reading apparatus comprising:

a white reference plate having a length which is no shorter than a main scanning width of the image sensor;

an auxiliary white reference plate which is smaller than the white reference plate;

a storing unit operable to store differential profile data indicative of a time-dependent change amount of a light intensity on the white reference plate detected by each of the light sensing elements corresponding to a time-dependent change amount of the light intensity of the light source, and differential profile auxiliary data indicative of a time-dependent change amount of a light intensity on the auxiliary white reference plate read by the image sensor as a representative light intensity of the light source corresponding to the time-dependent change amount of the light intensity of the light source; and a shading compensation unit operable to perform shading compensation, when a plurality of document sheets are successively read, such that in advance of reading a first document sheet, the white reference plate is read to acquire light intensity reference data indicative of the light intensities detected by the light sensing elements of the image sensor respectively, and the auxiliary white reference plate is read to acquire light intensity auxiliary reference data indicative of a representative light intensity of the light source, that after reading the first document sheet, the shading compensation is performed to the read data of the first document by the use of the light intensity reference data, that in advance of reading a second or subsequent document sheet, the auxiliary white reference plate is read to acquire latest light intensity auxiliary data indicative of the representative light intensity of the light source, and that after reading the second or subsequent document sheet, the shading compensation is performed to the read data of the second or subsequent document by calculating correction values on the basis of the differential profile data and a ratio of the difference between the light intensity auxiliary reference data and the latest light intensity auxiliary data to the differential profile auxiliary data, and correcting the light intensity reference data with the correction values.

2. The image reading apparatus as claimed in claim 1 wherein the shading compensation unit performs shading compensation to read data D of each picture element of a document sheet as corrected read data Ds by the use of a black reference value and a number of gradation levels for representing the read data on the basis of a compensation equation as follows $$Ds = \frac{(D - \text{black reference value}) \times \text{number of gradation levels}}{\left(\begin{array}{c}\text{light intensity reference data} - \\ \text{correction value} - \text{black reference value}\end{array}\right)}.$$

3. The image reading apparatus as claimed in claim 1 wherein
the representative light intensity obtained by reading the auxiliary white reference plate is an average value of the light intensities on the auxiliary white reference plate detected by the light sensing elements of the image sensor.

4. The image reading apparatus as claimed in claim 3 wherein
the average value of the light intensities is the average value of the light intensities on the auxiliary white reference plate detected by the light sensing elements within a predetermined area having widths both in the main scanning direction and in the secondary scanning direction.

5. The image reading apparatus as claimed in claim 1 wherein
when a predetermined condition is satisfied, the shading compensation unit updates the differential profile data and the differential profile auxiliary data by the use of the light intensity reference data which is recently acquired and the light intensity auxiliary reference data which is recently acquired.

6. The image reading apparatus as claimed in claim 5 wherein
just after updating the differential profile data and the differential profile auxiliary data, the shading compensation unit performs shading compensation by the use of the light intensity reference data which is recently acquired even for the second or subsequent document sheet.

7. The image reading apparatus as claimed in claim 5 wherein
the predetermined condition is the condition that a predetermined number of document sheets have been read, that a predetermined time elapses after starting the image reading process, or that the difference between the light intensity auxiliary reference data and the latest light intensity auxiliary data has exceeded the differential profile auxiliary data.

8. The image reading apparatus as claimed in claim 2 wherein
the shading compensation is performed separately for each of RGB channels.

9. The image reading apparatus as claimed in claim 1 wherein
when the white reference plate is read, the white reference plate is scanned along a plurality of lines in the secondary scanning direction, and
the average value of the light intensities detected by the light sensing elements along each of the plurality of lines in the secondary scanning direction is used as the light intensity detected by the light sensing elements of the image sensor respectively.

10. The image reading apparatus as claimed in claim 1 wherein
the differential profile data is calculated by detecting the change amounts of the light intensity on the white reference plate detected by the light sensing elements, and averaging the change amounts in the main scanning direction.

11. An image reading method for an image reading apparatus provided with a light source and an image sensor having a plurality of light sensing elements arranged in the main scanning direction, and operable to irradiate an object to be read with light emitted from the light source and read the reflected light from the object by the image sensor, the image reading method comprising:

a step of storing differential profile data indicative of a time-dependent change amount of the light intensity of a white reference plate, which has a length which is no shorter than a main scanning width of the image sensor, detected by each of the light sensing elements corresponding to a time-dependent change amount of the light intensity of the light source, and differential profile auxiliary data indicative of a time-dependent change amount of a light intensity on an auxiliary white reference plate, which is smaller than the white reference plate, read by the image sensor as a representative light intensity of the light source corresponding to the time-dependent change amount of the light intensity of the light source; and a step of performing shading compensation, when a plurality of document sheets are successively read, such that in advance of reading a first document sheet, the white reference plate is read to acquire light intensity reference data indicative of the light intensities detected by the light sensing elements of the image sensor respectively, and the auxiliary white reference plate is read to acquire light intensity auxiliary reference data indicative of a representative light intensity of the light source, that after reading the first document sheet, the shading compensation is performed to the read data of the first document by the use of the light intensity reference data, that in advance of reading a second or subsequent document sheet, the auxiliary white reference plate is read to acquire latest light intensity auxiliary data indicative of the representative light intensity of the light source, and that after reading the second or subsequent document sheet, the shading compensation is performed to the read data of the second or subsequent document by calculating correction values on the basis of the differential profile data and the ratio of the difference between the light intensity auxiliary reference data and the latest light intensity auxiliary data to the differential profile auxiliary data, and correcting the light intensity reference data with the correction values.

12. The image reading method as claimed in claim 11 wherein
in the shading compensation method, shading compensation is performed to the read data D of each picture element of a document sheet as corrected read data Ds by the use of a black reference value and the number of gradation levels for representing the read data on the basis of a compensation equation as follows $$Ds = \frac{(D - \text{black reference value}) \times \text{number of gradation levels}}{\left(\begin{array}{c}\text{light intensity reference data} - \\ \text{correction value} - \text{black reference value}\end{array}\right)}.$$

13. The image reading method as claimed in claim 11 wherein
the representative light intensity obtained by reading the auxiliary white reference plate is the average value of the light intensities on the auxiliary white reference plate detected by the light sensing elements of the image sensor.

14. The image reading method as claimed in claim 13 wherein
the average value of the light intensities is the average value of the light intensities on the auxiliary white reference plate detected by the light sensing elements within a predetermined area having widths both in the main scanning direction and in the secondary scanning direction.

15. The image reading method as claimed in claim 11 further comprising:
a step of updating, when a predetermined condition is satisfied, the differential profile data and the differential profile auxiliary data by the use of the light intensity reference data which is recently acquired and the light intensity auxiliary reference data which is recently acquired.

16. The image reading apparatus as claimed in claim 15 wherein
in the shading compensation step, just after updating the differential profile data and the differential profile auxiliary data, the shading compensation is performed by the use of the light intensity reference data which is recently acquired even for the second or subsequent document sheet.

17. The image reading method as claimed in claim 15 wherein
the predetermined condition is the condition that a predetermined number of document sheets have been read, that a predetermined time elapses after starting the image reading process, or that the difference between the light intensity auxiliary reference data and the latest light intensity auxiliary data has exceeded the differential profile auxiliary data.

18. The image reading method as claimed in claim 12 wherein
the shading compensation is performed separately for each of RGB channels.

19. The image reading method as claimed in claim 11 wherein
when the white reference plate is read, the white reference plate is scanned along a plurality of lines in the secondary scanning direction, and
the average value of the light intensities detected by the light sensing elements along each of the plurality of lines in the secondary scanning direction is used as the light intensity detected by the light sensing elements of the image sensor respectively.

20. The image reading method as claimed in claim 11 wherein
the differential profile data is calculated by detecting the change amounts of the light intensity on the white reference plate detected by the light sensing elements, and averaging the change amounts in the main scanning direction.

* * * * *